(12) United States Patent
Heinitz et al.

(10) Patent No.: US 7,332,730 B2
(45) Date of Patent: Feb. 19, 2008

(54) DEVICE AND METHOD FOR IMAGING A MULTIPLE PARTICLE BEAM ON A SUBSTRATE

(75) Inventors: Joachim Heinitz, Isserstedt (DE); Andreas Schubert, Niederrossla (DE)

(73) Assignee: Leica Microsystems Lithography GmbH, Jena (DE)

( * ) Notice: Subject to any disclaimer, the term of this patent is extended or adjusted under 35 U.S.C. 154(b) by 268 days.

(21) Appl. No.: 11/270,073

(22) Filed: Nov. 9, 2005

(65) Prior Publication Data

US 2006/0102853 A1    May 18, 2006

(30) Foreign Application Priority Data

Nov. 16, 2004   (DE)   ...................... 10 2004 055 149

(51) Int. Cl.
*G01N 23/00*    (2006.01)
*G01J 1/00*     (2006.01)
*H01J 37/30*    (2006.01)
*H01J 37/317*   (2006.01)

(52) U.S. Cl. ............................ 250/491.1; 250/492.22; 250/396 R; 250/398

(58) Field of Classification Search .............. 250/491.1
See application file for complete search history.

(56) References Cited

U.S. PATENT DOCUMENTS

| 4,147,937 A | | 4/1979 | Buelow et al. |
| 4,153,843 A | | 5/1979 | Pease |
| 4,433,384 A | * | 2/1984 | Berrian et al. .............. 382/145 |
| 4,477,729 A | | 10/1984 | Chang et al. |
| 4,853,870 A | | 8/1989 | Yasutake et al. |
| 5,144,142 A | | 9/1992 | Fueki et al. |
| 5,175,435 A | * | 12/1992 | Sakamoto et al. ....... 250/492.2 |

(Continued)

FOREIGN PATENT DOCUMENTS

DE          44 18 930 A1    12/1995

OTHER PUBLICATIONS

Berry, I.L. et al. Programmable Aperture Plate for Maskless High-Throughput Nonolithography. Journal of Vacuum Science & Technology. Nov./Dec. 1997, pp. 2382-2386, B 15(6), AVS Science & Technology Society, New York, NY.

*Primary Examiner*—David A. Vmore
*Assistant Examiner*—Bernard Souw
(74) *Attorney, Agent, or Firm*—Houston Eliseeva LLP (57) ABSTRACT

A device and a method for imaging and positioning a multiparticle beam on a substrate is disclosed. The device comprises a particle beam source with a condenser optic that produces a particle beam that illuminates the surface of an aperture plate. A multiplicity of individual beams are produced from the particle beam by means of the aperture plate, which are then projected by a projection system onto a substrate where they describe a beam base point. The substrate or target, respectively, is placed on a table that is movable along an x-coordinate and a y-coordinate, and that is provided with a laser path measurement system. The laser path measurement system relays positional data with a fixed clock rate to a synchronization and control device 50 that positions the beam base point along the x-coordinate and the y-coordinate via a beam tracking system, taking into account the corrective data and pixel phase, whereby precise staircase beam-to-table positioning is achieved across the entire substrate in spite of faulty table movement.

30 Claims, 7 Drawing Sheets

U.S. PATENT DOCUMENTS

| | | | |
|---|---|---|---|
| 5,528,048 A * | 6/1996 | Oae et al. | 250/492.22 |
| 5,614,725 A * | 3/1997 | Oae et al. | 250/492.22 |
| 5,920,077 A * | 7/1999 | Oae et al. | 250/492.22 |
| 5,977,548 A * | 11/1999 | Oae et al. | 250/397 |
| 6,118,129 A * | 9/2000 | Oae et al. | 250/492.22 |
| 6,403,973 B1 | 6/2002 | Takahashi et al. | |
| 6,486,479 B1 * | 11/2002 | Oae et al. | 250/492.2 |
| 6,515,409 B2 * | 2/2003 | Muraki et al. | 313/359.1 |
| 6,646,275 B2 * | 11/2003 | Oae et al. | 250/492.2 |
| 6,667,486 B2 | 12/2003 | Ohta et al. | |
| 6,774,379 B2 | 8/2004 | Hashimoto | |
| 2003/0025088 A1 * | 2/2003 | Oae et al. | 250/492.23 |
| 2003/0155534 A1 | 8/2003 | Platzgummer et al. | |
| 2006/0102853 A1 * | 5/2006 | Heinitz et al. | 250/491.1 |

* cited by examiner

DEVICE AND METHOD FOR IMAGING A MULTIPLE PARTICLE BEAM ON A SUBSTRATE

RELATED APPLICATIONS

This application claims priority to German patent application number DE 10 2004 055 149.9-54, filed Nov. 16, 2004, which is incorporated herein by reference in its entirety.

FIELD OF THE INVENTION

The invention relates to a device and a method for imaging a multi particle beam on a substrate. The device comprises a particle beam source that generates a particle beam. The surface of an aperture plate is illuminated by a particle beam via a condenser optic and generates a multiplicity of individual beams from the particle beam. A projection system projects the individual beams on a substrate, whereby the middle of the beam bundle defines a beam base point on the surface of the substrate. The substrate itself is placed on a table that is movable along a x-coordinate and along a y-coordinate and is provided with a laser path measurement system.

The invention further relates to a method for positioning a multi particle beam that consists of a multiplicity of individual beams that is formed by an aperture plate.

BACKGROUND OF THE INVENTION

Apart from the advantage that they possess high resolution, maskless particle projection systems (e-beam or ion beam writers) have the disadvantage of low productivity at the structural level of today, which is a result of the serial writing process of the particle beam. Because of this, renewed efforts are being made to increase the overall productivity of a particle projection system by employing a greater number of particle beams in parallel. One very promising approach consists in using a controllable aperture plate to deflect a multiplicity (up to several million) of partial beams that are together projected on the substrate.

U.S. Pat. No. 6,403,973 discloses a method for electron beam exposure and a device suitable for using this method. A substrate to be exposed is placed on a continuously moving table. In the process, the position of the table and the required beam position are determined and any deviations are corrected, making possible a highly precise, glitch-free adjustment of the individual exposure positions on the substrate. However, this device operates using a single electron beam. An aperture plate is not provided to generate a multiplicity of partial beams from the individual electron beams. Furthermore, exposure is not continuous, but rather takes place as a sequence of individual shots.

U.S. Pat. No. 4,853,870 also discloses an electron beam exposure system that takes into account the position of the table during exposure and corrects any potential deviation via a two-step excursion of the electron beam. Here, too, only a single electron beam is used for exposure by keying and reading the beam by means of a sequence of shots.

U.S. Pat. No. 4,477,729 describes an electron beam exposure system that works by using a continuous writing system. Here, the structures to the generated are exposed as a sequence of adjacently lying partial structures, whereby the set position of the table is given by a corresponding sequence of closely adjacent reference positions of the partial structures. In this system, too, corresponding correction is carried out between the current table position and the current writing position of the electron beam. The forward transfer of a partial field of action to the next, however, presupposes a blanking of the particle beam. In addition, this system uses only a single particle beam.

A further exposure arrangement and method using a single electron beam is disclosed in U.S. Pat. No. 4,147,937. The described arrangement also works by tracking the beam-to-table position on the basis of a positional measurement system. However, exposure is done by controlling specified set positions in a step-and-go mode.

U.S. Pat. No. 4,153,843 discloses an exposure system with several beams. Here, a two-dimensional array with several openings is provided in the beam path of an electron beam exposure system. The surface of the array is illuminated by the electron beam and imaged in miniature on a substrate. Individual beams can be switched off by means of the aperture plate so that these do not reach the substrate. The aperture plate thus ensures that the dosage of electrons on the substrate can be regulated at each addressed position of the electron beam so that the proximity effect can be corrected. Correction of table deviation and corresponding control of the electron beam are not disclosed.

U.S. Pat. No. 5,144,142 discloses a particle beam system that comprises an aperture plate to produce the corresponding partial beams. The aperture plate array comprises n lines and m columns of openings that are arranged in a two-dimensional fashion on a substrate. A pair of deflection electrodes is arranged at each of the openings. Furthermore, n- and m-bit-long shift registers are provided on the substrate in order to direct the deflecting voltage corresponding to the pattern data to the m pairs of electrodes of each line. Exposure occurs by shifting the pattern data through the aperture array while simultaneously deflecting the beam bundle. Here, the current table position determined by a laser interferometer is compared with the set data position, and the difference is taken into account during deflection. A device for synchronizing the table system with the shifts in the aperture plate is, however, not disclosed.

U.S. patent application US 2003/0155534 A1 discloses a maskless exposure system for particle beams. A multi beam is formed by means of a stack of aperture plates, whereby a blanking plate with an integrated shift register and storage circuitry enables level adjustment of each partial beam in synchrony with the scanning movement of the table system. In order to fix the pixel images during exposure on the moving substrate, a deflection system controlled by sawtooth voltage is proposed. A technical solution for synchronizing table movement with the shifts in the blanking plate and the deflection movement of the multi particle beam is, however, not disclosed.

The article "Programmable Aperture Plate for Maskless High-Throughput Nanolithography" by Berry et al.; J. Vac. Sci. Technol. B 15(6), November/December 1997; pp. 2382-2386, discloses a programmable aperture array that comprises 3000×3000 apertures that can be electronically individually adjusted and therefore switched on and off in order to achieve dynamic control of beam throughput. The pattern to be exposed is loaded successively from one side into the aperture array and pushed through to the other side by means of integrated shift steps. The wafer to be written on is moved in synchrony to it. Control or correction of the current table position is not disclosed in this article.

All known publications that treat beam tracking on the basis of a laser path measurement system to determine table position proceed from the principle of a fixed writing field. Beam tracking compensates for the deviation in the current table position from a specified set position that is indicated by the laser path measurement system and fixes the midpoint of the current writing field. Because the maximum size of the writing field is limited as a result of imaging errors of the particle optic, the surface of the substrate is exposed by arraying a multiplicity of writing fields (with overlaps under certain circumstances). A blanking of the total beam is required for repositioning the writing fields; uninterrupted writing of a strip across the entire substrate is therefore not possible.

The documents that mention aperture plate arrays either do not go further into the problem of beam-to-table positioning, or they provide for beam tracking that is independent of pixel shifting in the aperture array. In the latter case, the aperture array can only be used to scan across the breadth of a fixed writing field, as just mentioned. Otherwise, systematic position errors occur as a result of a lack of synchronization between the table system and the aperture plate system.

Straying of a shift phase from the current position values of the moving table system, i.e., upon reaching the subsequent set position, in which the aperture array is advanced by one phase does not represent a solution to the problem because intolerable time—and therefore dosage—fluctuations occur as a result of the imprecise table travel.

SUMMARY OF THE INVENTION

The underlying object of the invention is to position a structured particle beam precisely by means of an aperture array onto a substrate that is located on a table that is moved continuously along an x-coordinate and a y-coordinate.

This object is solved by a device with the characteristics contained in claim 1.

A further underlying object of the invention is to produce a method by which a structured pixel beam can be positioned precisely on a moving substrate by an aperture array, whereby the substrate is located on a table that is moved continuously along an x-coordinate and a y-coordinate.

This object is solved by a method with the characteristics contained in claim 14.

On the one hand, the invention is characterized in that the device and the method can correct sequencing errors of the table. Furthermore, the working principle of an aperture array that advances the latent pixel image by one pixel scan □p, column by column at a shift frequency fS, requires a staircase change in beam position on the substrate. A staircase course with 107 steps without interruption of continuous exposure and with absolute precision in the nanometer range must be generated at an excursion of the table of 250 mm and a pixel scan of □p=25 nm. This is achieved by the present invention. Furthermore, in order to achieve a required exposure dosage, the shift frequency fS can be fine-adjusted up to a range of several 10's of MHz without interfering with the functioning of the device with regard to precise positioning or synchronization.

The device for imaging a multiparticle beam on a substrate comprises a particle beam source, a condenser optic, an aperture plate system the surface of which is illuminated by the particle beam and generates a multiplicity of individual beams from the particle beam, as well as a projection system with which the particle beams can be exposed in miniature on a substrate and there define a beam base point. The substrate itself is placed on a table in the position of which is determined or monitored by a laser path measurement system, and that can be moved along the x-coordinate and the y-coordinate. The laser path measurement system delivers positional data with a fixed clock rate to a synchronization and control device that positions the beam tracking system along the x-coordinate and the y-coordinate via a multichannel beam base point system that takes into account corrective data and the pixel phase.

A set position generator that sets a highly linear shift in the set position of the beam base point along the x-coordinate and the y-coordinate is driven by the phase of the laser path measurement system. The set position generator comprises a set position register to which a first multiplexer and a second multiplexer are connected in series via a digital adder. The set position register is loaded with the start position of the exposure strip before beginning exposure via the first multiplexer. From start time $t_S$, the set position register is incremented cyclically at a step value Δn by switching the second multiplexer.

The synchronization and control device works synchronously in phase, whereby the phase frequency $f_{SNF}$ corresponds to the maximum measurement rate of the laser path measurement system. A glitch-free digital-to-analog converter is provided at the exit port of the synchronization and control device to control the beam tracking system. A correction value is generated from the difference between the set position generated and the positional data from the laser path measurement system, which is then transformed to analog via the beam tracking system, which zeros the deviation between the current position and the desired position of the beam base point.

The synchronization and control device further comprises a sawtooth generator that is implemented as a digital function generator and keeps the beam base point on the substrate constant while a pixel is exposed for $1/f_S$. The sawtooth generator comprises a digital data storage phase generator, a back-coupled digital accumulator with a start value register and a step register, as well as a fast digital-to-analog converter. From the phase generator, a phase signal with an integral multiple of n of the ground frequency $f_S$ is supplied synchronously with the ground frequency $f_S$. The sawtooth generator generates a sawtooth signal via digital-to-analog conversion of a digital word in the accumulator, whereby this signal is set to the value $a_0$ of the start register and is accumulated by the value Δa of the step register with each positive flank of the phase multiple n $f_S$. Furthermore, a digital subtracter is integrated into the sawtooth generator, which at start point $t_S$ of the exposure subtracts the current value of the accumulator from the value $a_0$ in the start value register.

The entire synchronization and control device is driven by a stable quartz mother phase generator, from which the phase frequency $f_{SNF}$ of the beam tracker as well as the input frequency $f_{in}$ of the DDS phase generator is derived.

The method for positioning a multiparticle beam formed by an aperture plate, consisting of a multiplicity of individual beams, advantageously comprises the following steps:

Projecting a multiplicity of individual beams via a projection system onto a substrate, whereby a beam base point is defined on the substrate.

Moving the table in a specified direction, whereby a laser path measurement system determines table positions x and y, and relays the values to a control device to which a multi-step beam tracking system is attached. Supported by the laser path measurement system, generation of a highly linear constant shift between the base point of the particle beam and the table.

Generating a shift phase for the aperture plate system, whereby its frequency $f_S$ can be selected by a DDS switch over a wide range and with high precision.

Production of a sawtooth signal precisely the same as the frequency $f_S$ with the help of a digital sawtooth generator, which deflects the multibeam via a fast digital-to-analog converter and a step of the beam tracking system such that the beam base point is described on the substrate over the course of a pixel exposure time $1/f_S$.

Adjusting the offset of the sawtooth signal by subtracting the current accumulator value from the start value of the sawtooth generator at time $t_S$ at which exposure is started in order to compensate for the phase shift between the beam tracking phase $f_{SNF}$ and the shift phase $f_S$, and to achieve precise positioning of the first pixel image.

Further advantageous developments of the invention may be found in the subclaims.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

The diagrams show schematically the object according to the invention, which will be described below on the basis of the figures. They show.

DETAILED DESCRIPTION OF THE PREFERRED EMBODIMENTS

Figure 1:
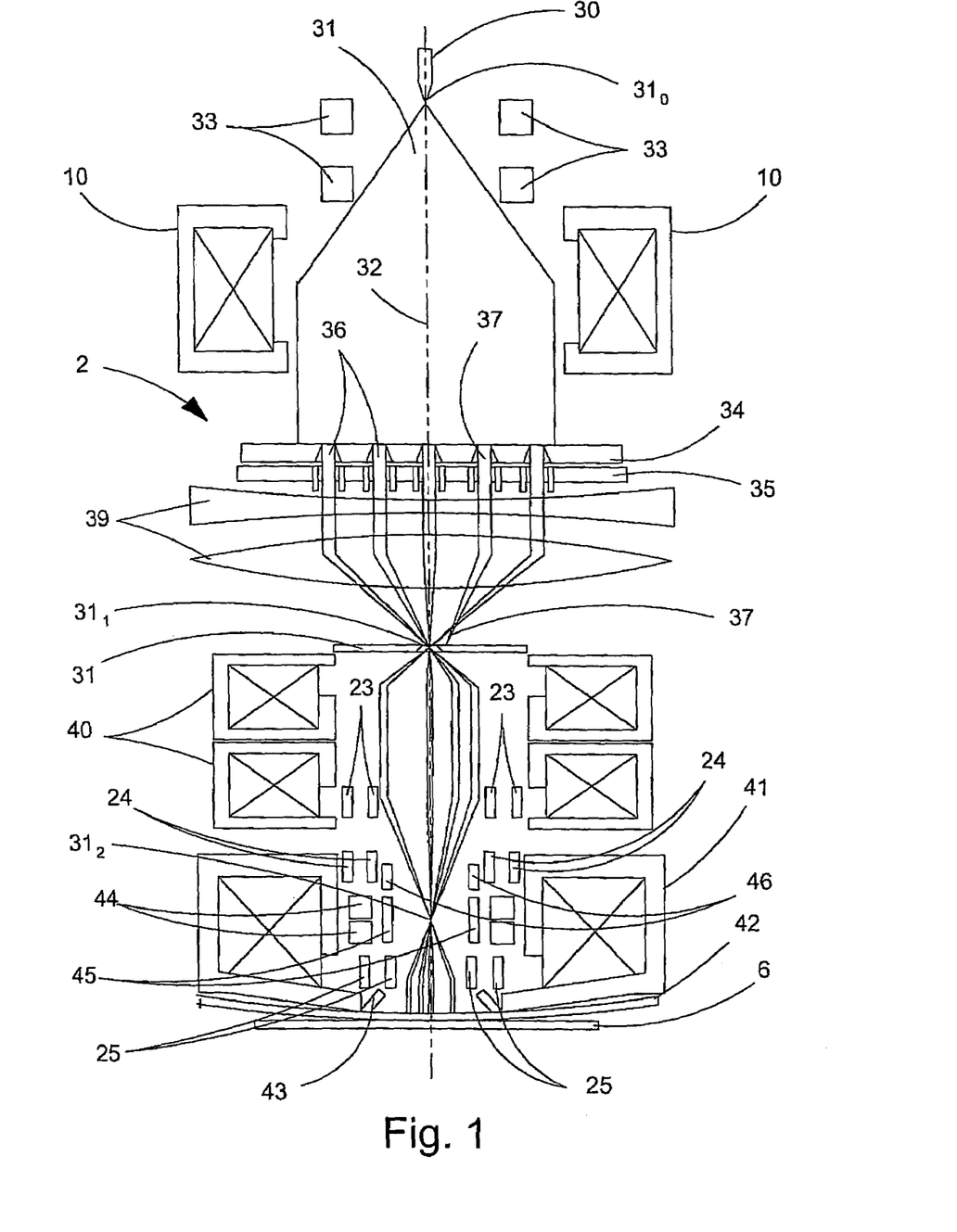
FIG. 1 a schematic representation of the construction of an entire electron beam lithography system.

FIG. 1 shows the principal beam path of a particle projection system 2. The particle projection system 2 is then described, the particles in this case being electrons. However, this restriction to electrons should in no way be interpreted as a limitation of the invention. It is obvious that the present invention can also be implemented with particles other than electrons. An electron beam 31 that is produced by an electron cannon 30 spreads out in the direction of an electron optical axis 32. The electrons emitted by the electron cannon 30 exhibit a source crossover $31_0$. The electron cannon 30 is connected to a beam centering device 33 that aligns the electron beam 31 symmetrically around the optical axis 32. After the beam centering device, the electron beam 31 passes through an illumination condenser 10, which forms a parallel beam from the initially divergent electron beam. The beam formed by the illumination condenser 10 possesses a diameter, across which the intensity is homogeneously distributed. An aperture plate 34 with a multiplicity of openings to produce many parallel beam bundles 36 is provided after the illumination condenser 10. In the direction of spread of the beam bundle 36 toward the target 6 there follows a deflection plate 35 that possesses a multiplicity of beam deflector units. After the deflector plate 35 there follows an acceleration lens 39 that increases the energy of the electrons in the electron beam and then produces a first intermediate image of the crossover $31_1$ at the site of the aperture plate 38. All individual crossovers of the particle beam bundle 36 are created at almost the same site, namely at the aperture opening of the aperture plate 38. The diameter of the opening of the aperture plate 38 is selected such that almost all electrons of the undeflected beam bundle 36 may pass through the aperture plate 38. Individual beams 37 that have experienced a change in direction as a result of the aperture plate 35 are stopped at the aperture plate 38 because their crossover image was not produced at the site of the aperture plate opening. Over the further trajectory of the beam, there is at least one magnetic lens 40 to miniaturize the image from the aperture plate 34 on the target 6. Two magnetic lenses 40 are shown in the embodiment of the invention described here. During imaging, a second intermediate image of the crossover $31_2$ is produced. Before the undeflected beam bundles 36 reach the target 6 that can, for example, be a wafer, they pass through an objective lens 41. The objective lens 41 is provided with a multiplicity of elements. Two deflectors 45 and 46 are provided before and after the second crossover $31_2$ of the electron beam 31. The deflectors 45, 46 serve to deflect, and to determine the position of the electron beam 31 or the multiplicity of undeflected beam bundles 36 in the target 6. The two independently controllable deflection systems 45, 46 are advantageously used to optimize separate production of slow and fast deflection processes. Fast deflection processes in the MHz to GHz frequency range are required, for example, in order, by means of sawtooth deflection, to hold constant the position of the miniaturize aperture plate 34 on the identically shaped moved target 6 for the duration of an exposure step, and subsequently to jump to the next exposure point very quickly. Because adjacent pixels are typically located less than 100 nm away, the fast deflection system 46 is preferably implemented as an electrostatic system. In order to compensate for low-frequency positional deviations of the target 6 from the corresponding movement in the range of several micrometers, a slow but highly precise magnetic deflection system 45 is preferably used. Furthermore, stigmators 44 are provided that are preferably implemented as multilayer magnetic coil systems in order to compensate for astigmatism and distortion in the optical column, which are conditional on manufacturing tolerances and adjustment errors. The objective lens 41 has a scanning hypsometry system 42 at the target or beam base point of the electron beam at the target 6. The hypsometry system serves to detect unevennesses in the target 6 (e.g., wafer) as well as height fluctuations that can be caused by the moving table. A detector is located close to the beam base point for the particles scattered back from the target 6. This detector serves to determine the position of marks on the target 6 for the purpose of covering several exposure planes, and to calibrate the control elements of an exposure apparatus, respectively. Furthermore, there are three pairs of corrective lenses 23, 24, 25 in the lower region of the projection system of the corpuscular optical column. The corrective lenses 23, 24, 25 serve to dynamically correct the focus, the size of the image field, and the rotation of the image field during exposure of the constantly moved target 6. The corrective lens system 23, 24, 25 enables the correction of errors that may be brought about by height fluctuations in the target as well as by variable spatial charges in the column region.

Figure 2:
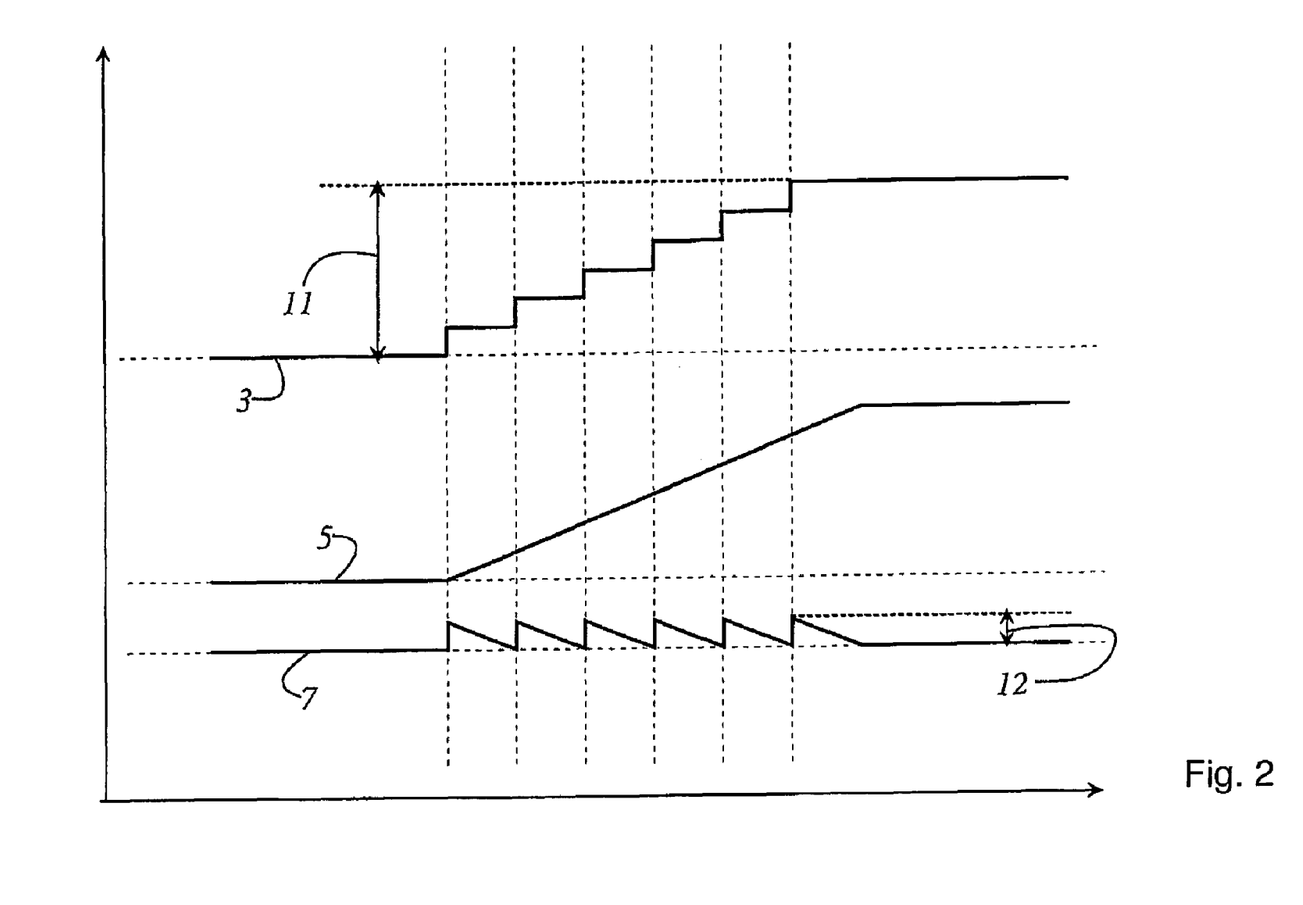
FIG. 2 a representation of the generation of a staircase curve trace.

FIG. 2 shows in principle how a staircase curve trace 3 can be generated by overlaying an ascending/descending ramp with a fast sawtooth signal 7. In this case, the ramp 5 determines the integral linearity of the signal, but needs to possess only little bandwidth. The higher frequency sawtooth signal 7 determines the differential precision of the staircase, but in comparison to the total height 11 of the staircase 3 has only a low amplitude 12. The staircase curve trace 3 describes the desired change in the beam position on the substrate or target 6, respectively. With an excursion of the table of approximately 250 mm at a pixel scan of $\Delta p=25$ nm it is necessary to generate a staircase curve trace 3 with $10^7$ steps without interrupting the exposure in progress, and with absolute precision in the nanometer range. In order to position the progressive pixel images of the aperture plate 34, it is possible to accomplish this in two steps according to FIG. 2. First, by means of the table system including beam tracking, which produces a highly linear constant beam-to-table shift with the help of a laser path measurement system 20. This highly linear constant beam-to-table shift is represented as an ascending/descending ramp 5 in FIG. 2. The second step is accomplished by a fast corrective deflection system that enables sawtooth-shaped deflection in a few scanning steps $\Delta p$ in synchrony with the pixel phase. The sawtooth deflection is represented by the sawtooth signal 7 in FIG. 2.

Figure 3:
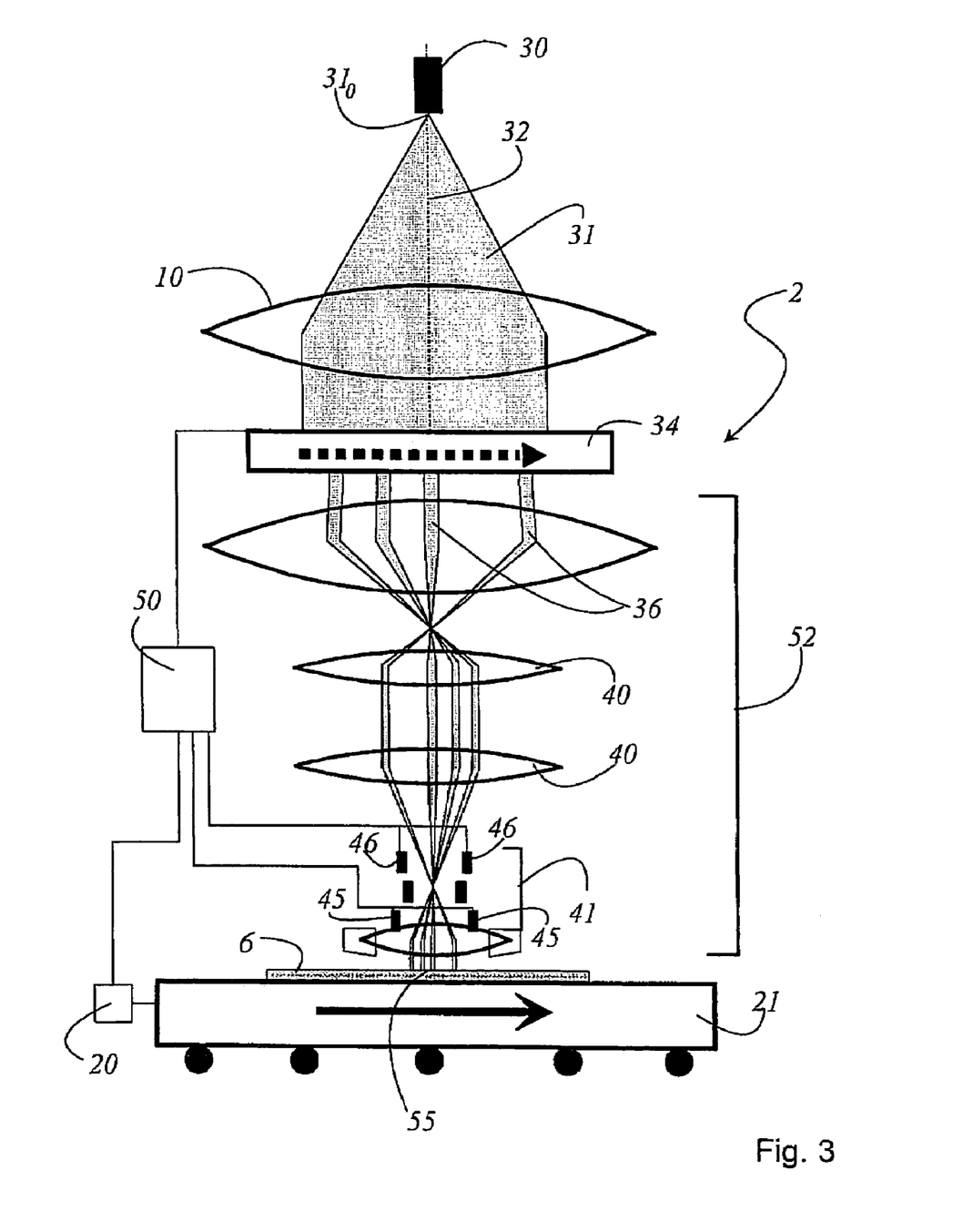
FIG. 3 an exposure apparatus with an aperture plate array comprising a table system and a beam tracker.

FIG. 3 shows a particle projection system 2, whereby a table 21 that carries the substrate 6 and is movable along the x-coordinate and the y-coordinate is measured by means of a laser path measurement system 20. The laser path measurement system 20 relays positional data about the table by means of a fixed clock rate to the synchronization and control device 50. An electron beam source 30 emits an electron beam 31 that exhibits a source crossover $31_0$. The electron beam spreads out along the optical axis 32. The illumination condenser 10 forms a parallel beam from the initially divergent electron beam 31. The parallel beam strikes an aperture plate 34 that is provided with a multiplicity of openings to produce many parallel beam bundles 36. The particle beam optical exposure system 52 comprises at least two magnetic lenses 40 and an objective lens 41. During exposure of the target 6 or of the substrate, respectively, it is important to move a beam base point 55 produced by the exposed particle beam on the substrate at a constant velocity in a specified direction. This direction of the beam base point 55 must be coordinated with the linear movement of the movable table 21 along the x-coordinate and the y-coordinate. The synchronization and control device 50 is provided for this purpose.

Figure 4:
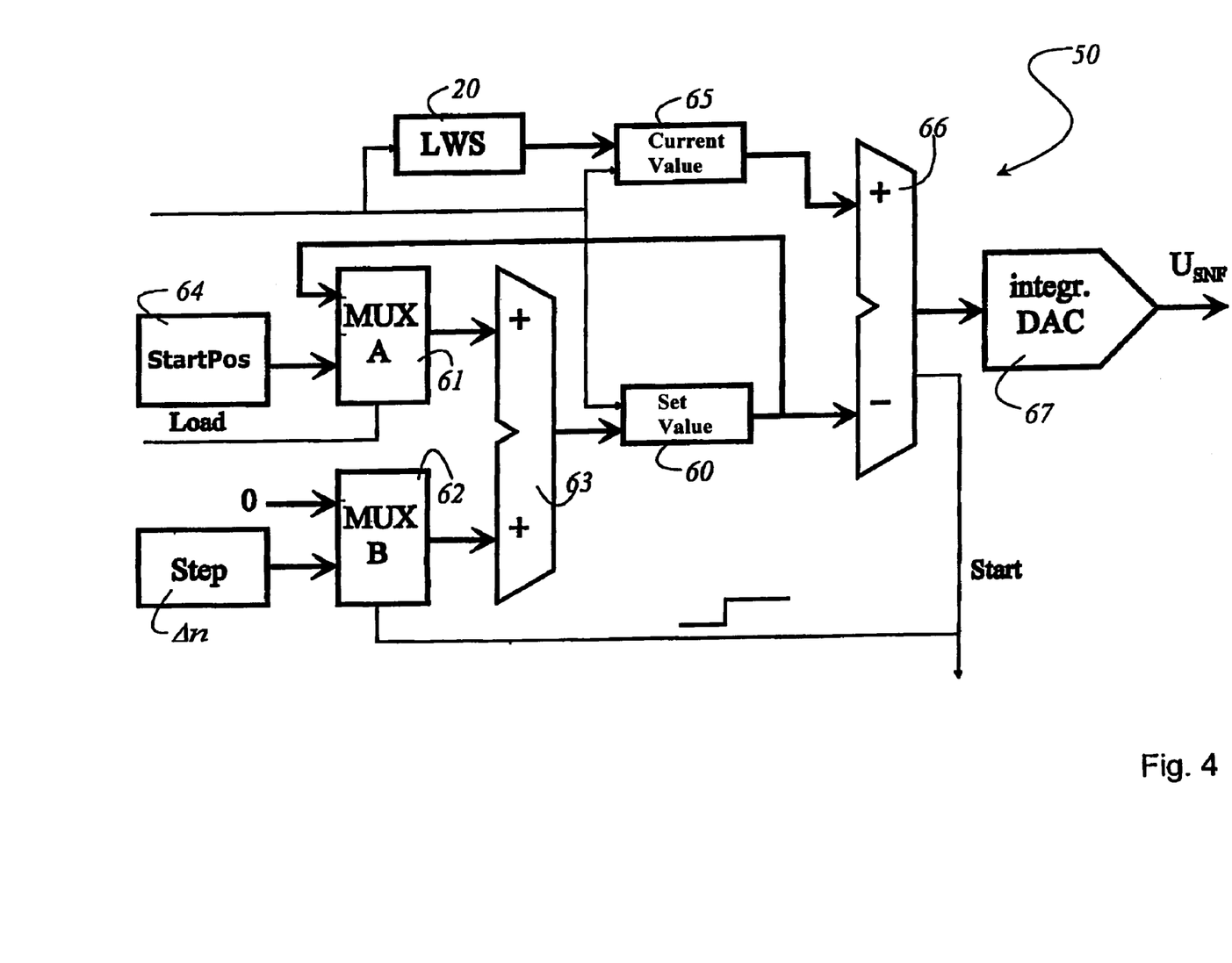
FIG. 4 a schematic representation of an automated logic diagram of the modified beam tracker.

The design of the synchronization and control device 50 is represented in FIG. 4. A set position generator is driven by the phase of the laser path measurement system 21, which establishes a highly linear shift in the set position of the beam base point 55 at the start point $t_S$ along the x-coordinate and the y-coordinate. The set position generator comprises a set position register 60 to which a first multiplexer 61 and a second multiplexer 62 are connected in series via a digital adder 63. The set position register 60 is loaded with the start position 64 of the exposure strip via the first multiplexer 61 before beginning exposure of the target 6. From start time $t_S$, the set position register 60 is incremented cyclically at a step value $\Delta n$ by switching over to the second multiplexer 62. The current position of the table 21 that is movable along the x-coordinate and the y-coordinate is relayed by the laser path measurement system to a current point register 65. The content of the current point register 65 and the content of the set position register are then relayed to a subtracter 66. The subtracter 66 is connected with a digital-to-analog converter 67 that is implemented as an integrator. Depending on the difference between the current table position that is stored in the current point register 65 and the value in the set position register 60 current is applied to the controller of the beam tracking system, which corrects the measured deviation via the beam tracking/deflection system after an integration time of $1/f_{SNF}$. It is absolutely necessary for beam tracking that the synchronization and control device 50 be phase-synchronous, whereby the phase frequency $f_{SNF}$ corresponds to the maximum measurement rate of the laser path measurement system 20. The value $\Delta n$ represents precisely the number of laser path measurement increments of the laser path measurement system 20 that must ideally be accrue at a specified velocity of the table 21 movable along the x-coordinate and the y-coordinate during the time frame $1/f_{SNF}$. To avoid an accumulation of errors, $\Delta n$ must be entered into the digital calculation with a high level of precision, i.e., a large number of decimal places.

Figure 5:
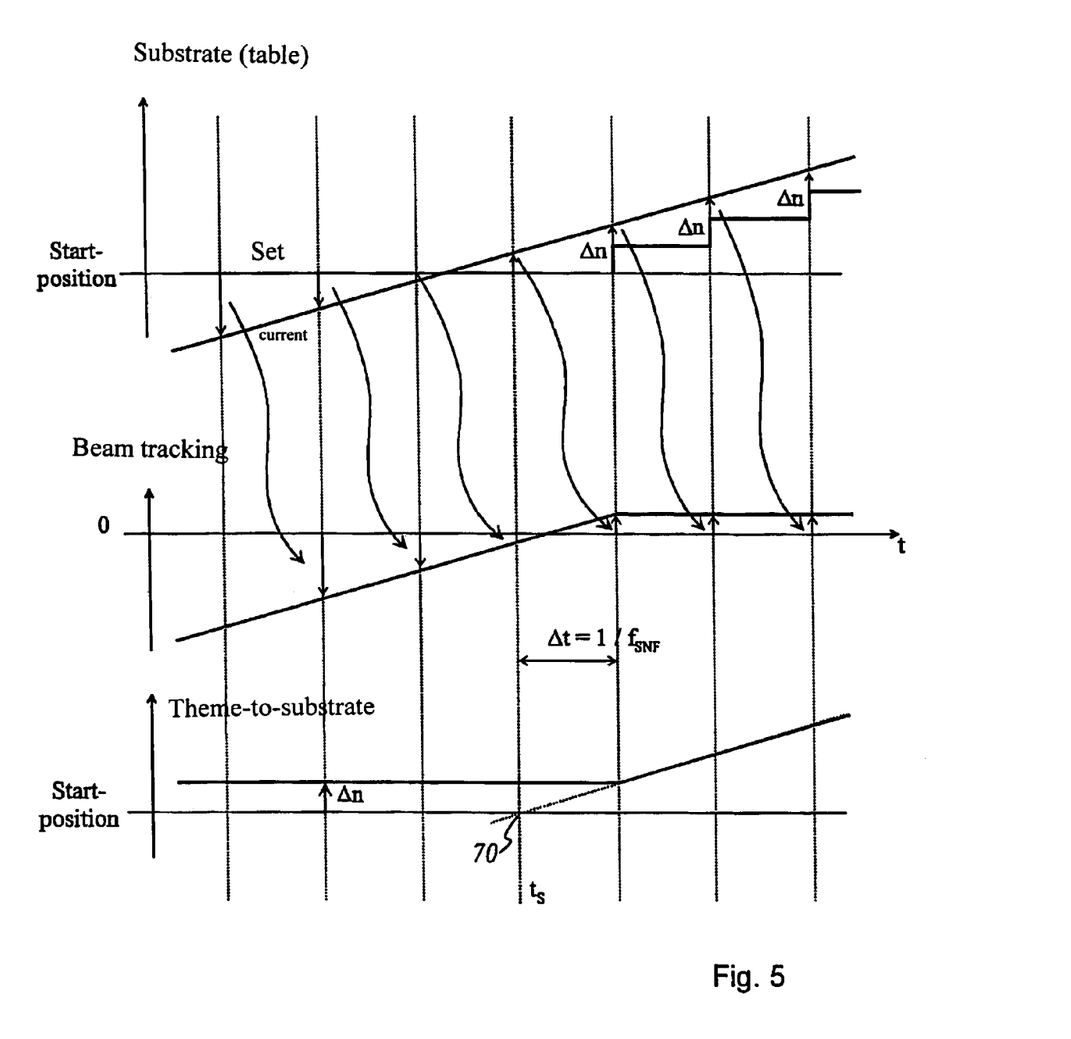
FIG. 5 the trajectory of beam-to-substrate positioning.

FIG. 5 represents the operational characteristics of the modified beam tracking system. Here, it is presumed that the table 21 that is movable along the x-coordinate and the y-coordinate moves at a constant velocity toward the start point of the exposure after an acceleration phase in the capture region of the beam tracking system. The absolute position of the start point is stored in the set position register 60. Before reaching this point, the beam tracking works in the manner already known. Beam tracking attempts to position the beam on the start point, whereby a systematic deviation of $\Delta n$ remains because of the delay in correction. If the start point 70 is reached or exceeded at a time $t_S$, a start signal is triggered, which activates the accumulator of the synchronization and control device 50 by switching the multiplexer 62. The systematic deviation disappears by successive addition of $\Delta n$ to the set position. In addition, the beam tracker corrects the positional error of the table 21 to the start time point during the cycle after $t_S$, and changes its deflection accordingly not only, or only then, respectively, when deviations from the ideal linear curve of excursion occur in the course of the table 21 that is movable along the x-coordinate and the y-coordinate. This achieves two tasks simultaneously. First, a highly linear beam-to-table shift is achieved with the laser path measurement system 20, and second, the start point of this shift is adjusted to a specified start point for exposure of the target 6.

A further variant in the operational characteristics is achieved in the case of a table 21 that is not moved in the positioning direction. In this case, beam tracking first statically compensates for the measured deviation from the start position and works from start time $t_S$ as a laser path measurement supported scanning generator.

Figure 6:
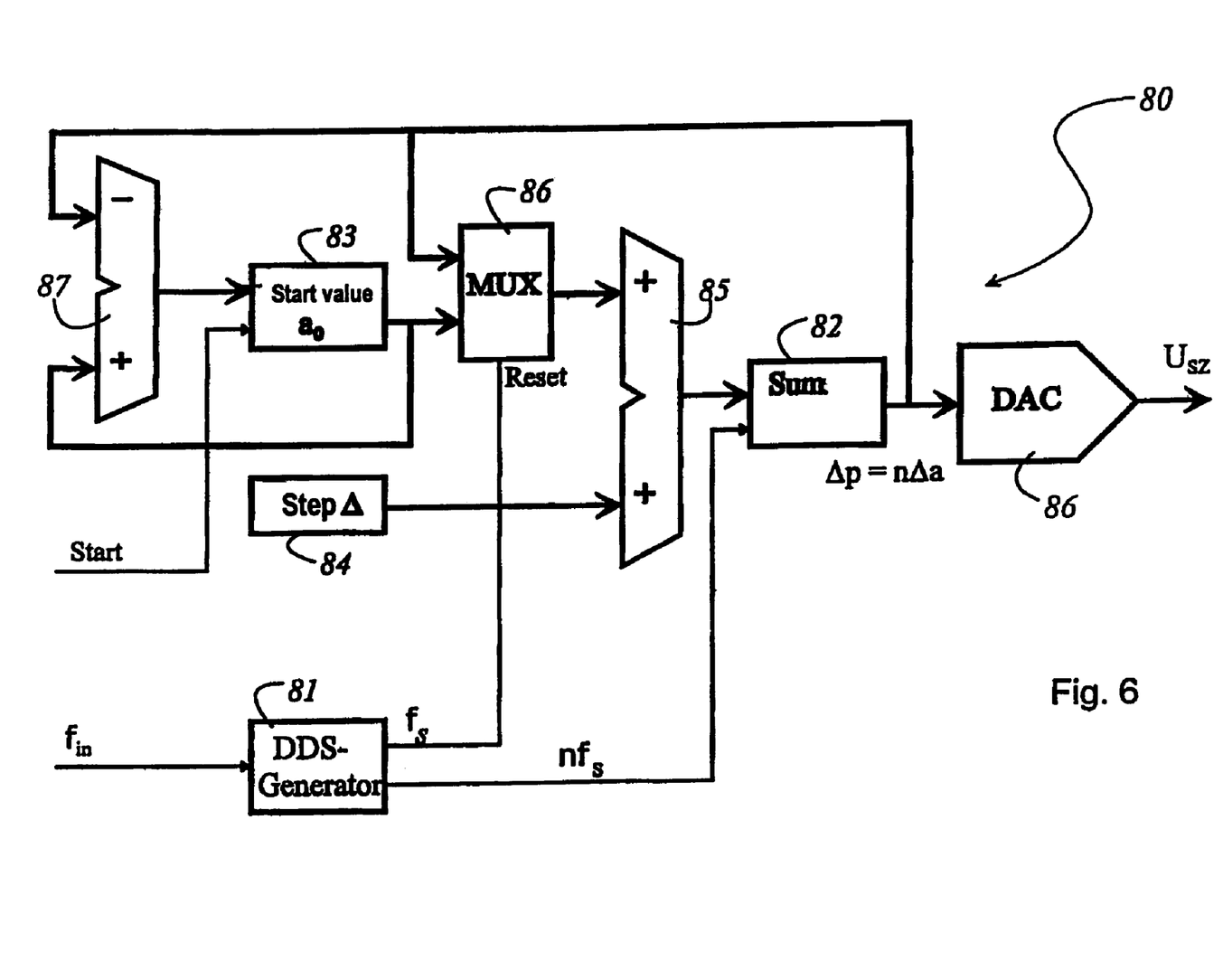
FIG. 6 an automated logic diagram of the sawtooth generator according to the invention.

FIG. 6 shows an automated logic diagram of the sawtooth generator 80. The synchronization and control device 50 comprises a sawtooth generator 80 that is implemented as a digital function generator and that maintains the beam base point constant on the substrate during exposure of a pixel image. In order to keep the beam position unchanged relative to the table for the time period needed for exposing a pixel image, two main requirements are made of the sawtooth generator 80 that is needed for driving the fast correction system. The first requirement is that the frequency of the sawtooth must correspond precisely to the pixel shift frequency $f_S$ in the aperture array 34. The second requirement is that the amplitude via the deflection system results in a beam deflection of exactly $\Delta p$. The pixel shift frequency $f_S$ is, in correspondence with the frequency range, precision adjustment, and stability requirements of the state-of-the-art, produced according to the principle of direct digital synthesis (DDS). In other words, the sawtooth generator is comprised of a DDS phase generator 81, to which is attached a digital back-coupled accumulator 82. In addition, the sawtooth generator comprises a start point register 83 and a step register 84. The step register is connected to an adder 85. The start point register 83 is connected to the adder 85 via a multiplexer 86. The sawtooth generator 80 further possesses a fast digital-to-analog converter 86. Synchronous to the ground frequency $f_S$, the DDS phase generator 81 also delivers a phase signal with an integral multiple n $f_S$. The sawtooth signal is created by digital-to-analog conversion of the digital word in the accumulator 82, whereby this is set to the value $a_0$ in the start register 83 for each positive flank of the pixel phase $f_S$, and is accumulated with each further flank of the phase multiple n $f_S$ of the value $\Delta a$ of the step register 84. An ascending or a descending sawtooth must be generated, depending on the direction of excursion of the table 21, and must be achieved by adjusting for positive or negative values of $\Delta a$. This results in a step signal with n steps that is precisely synchronized with the pixel shift frequency, and at n>10 this approximates a sawtooth signal with good precision. The amplitude of the signal can be digitally adjusted with great precision by selecting the step height $\Delta a$. Both the update rate $f_{SNF}$ of the beam tracker and the initial frequency $f_{in}$ of the DDS phase generator 81 are derived from a common stable quartz mother generator. This guarantees that no positional shifts can occur as a result of frequency were phased deviations when exposing a strip on the target 6. Both frequencies $f_{SNF}$ and $f_S$ have frequencies that are different from each other. This leads to the circumstance during sequential writing on a multiplicity of strips on the target 6 to an unacceptable positional jitter of the strip start point on the order of $\Delta p$. A digital subtracter 87, which at start time $t_S$ subtracts the current value of the accumulator 82 from value $a_0$ in the start register 83, is integrated in the sawtooth generator 80 for the purpose of adaptive phase equalization. Because the new value $a_0$ specifies the zero point of the sawtooth curve during the next flank of the pixel phase shift, this is then shifted by a certain offset amount.

Figure 7:
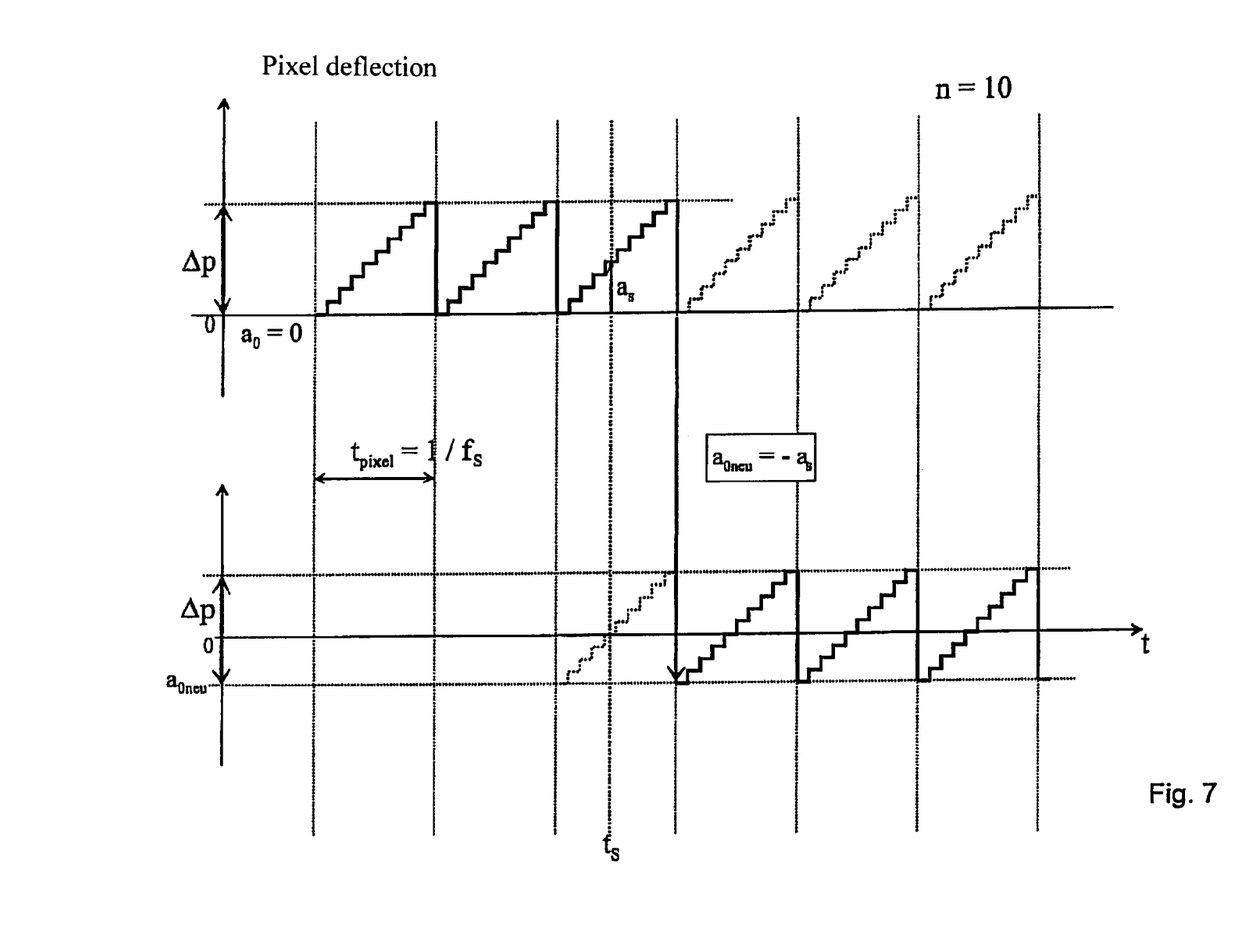
FIG. 7 a schematic representation of the principle of adaptive phase compensation.

The principle of adaptive phase equalization is represented in FIG. 7, whereby the start value $a_0$ was first assumed to be equal to zero. Because the new value specifies the zero point of the sawtooth curve during the next flank of the pixel phase shift, this than shifts by a certain offset amount $a_{0\ new}$. The result is that the zero accumulator value is always reached at one and the same point in time for all phase positions of $f_S$, and as a result the starts of the strips are really positioned in line with the target.

While this invention has been particularly shown and described with references to preferred embodiments thereof, it will be understood by those skilled in the art that various changes in form and details may be made therein without departing from the scope of the invention encompassed by the appended claims.

What is claimed is:

1. Device for imaging a multiparticle beam on a substrate, with a particle beam source that generates a particle beam; an aperture plate, the surface of which is illuminated by the particle beam, and which generates a multiplicity of individual beams from the particle beams that are then projected by a projection system on a substrate, where they describe a beam base point, whereby the substrate is placed on a table that is movable along an x-coordinate and a y-coordinate, and that is provided with a laser path measurement system, wherein the laser path measurement system relays point data with a fixed clock rate to a synchronization and control device and positions the beam base point along the x-coordinate and the y-coordinate via a multichannel beam tracking system, taking into account corrective data and the pixel phase.

2. Device according to claim 1, wherein the phase of the laser path measurement system drives a set position generator, which generates a highly linear shift in the set position of the beam base point along the x-coordinate and the y-coordinate from a start point $t_S$.

3. Device according to claim 2, wherein the set position generator comprises a set position register to which a first multiplexer and a second multiplexer are connected in series via a digital adder.

4. Device according to claim 3, wherein the set position register contains a value which, from start time $t_S$ is incremented cyclically at a step value $\Delta n$ by switching the second multiplexer, whereby the set position register is loaded with the start position of an exposure strip via the first multiplexer before beginning exposure.

5. Device according to claim 1, wherein the synchronization and control device works in synchronous phase, whereby a phase frequency $f_{SNF}$ corresponds to the maximum measurement rate of the laser path measurement system.

6. Device according to claim 1, wherein a digital-to-analog converter is provided at the outlet of the synchronization and control device.

7. Device according to claim 6, wherein a corrective value results from the difference between the generated set position and the point data of the laser path measurement system, which compensates to zero the deviation between the current point and the set position of the beam base point.

8. Device according to claim 1, wherein the synchronization and control device comprises a sawtooth generator that is implemented as a digital function generator and holds the beam base point constant on the substrate during exposure of a pixel image.

9. Device according to claim 8, wherein the sawtooth generator is comprised of a DDS phase generator, a back-coupled digital accumulator with a set position register and a step register, and a fast digital-to-analog converter.

10. Device according to claim 9, wherein the phase generator delivers a phase signal with an integral multiple n of the ground frequency $f_S$ synchronous to the ground frequency $f_S$.

11. Device according to claim 9, wherein a digital subtracter is integrated in the sawtooth generator, and wherein the start point $t_S$ of the subtracter subtracts the current value of the accumulator from value $a_0$ in the start register.

12. Device according to claim 1, wherein the periodicity and the phase of the sawtooth generator and the pixel phase are the same.

13. Device according to claim 1, wherein a common stable quartz mother phase generator is provided, from which the phase frequency $f_{SNF}$ of the beam tracker as well as the input frequency $f_{in}$ of the DDS phase generator are derived.

14. Method for positioning a multibeam particle comprising a multiplicity of individual beams formed by an aperture plate system, characterized by the following steps:

Projecting a multiplicity of individual beams via a projection system onto a substrate, whereby a beam base point is defined on the substrate;

Moving the table in a specified direction, whereby a laser path measurement system determines table positions x and y, and relays the values to a control device to which a multi-step beam tracking system is attached; and Generating a shift phase of a specified frequency $f_S$ for the aperture plate system via the control device, whereby the frequency $f_S$ can be used to fine-position the pixel images.

15. Method according to claim 14, wherein a highly linear constant shift is produced between the base point of the particle beam and the table with a beam tracker supported by the laser path measurement system.

16. Method according to claim 15, wherein the control device comprises a set position register, whereby a first multiplexer and a second multiplexer are connected to the set position register.

17. Method according to claim 16, wherein the set position register contains a value, which from start time $t_S$ is incremented cyclically from a step value $\Delta n$ by switching the second multiplexer, whereby the set position register is loaded with the start position of an exposure strip via the first multiplexer before beginning exposure.

18. Method according to claim 15, wherein the set position register is a back-coupled accumulation register.

19. Method according to claim 14, wherein the control device works in synchronous phase, whereby a phase frequency $f_{SNF}$ corresponds to the maximum measurement rate of the laser path measurement system.

20. Method according to claim 14, wherein a digital-to-analog converter is provided at the outlet of the control device to control the beam tracking system.

21. Method according to claim 20, wherein the digital-to-analog converter is implemented as an integrator.

22. Method according to claim 21, wherein the electrical current with which the measured deviation is corrected via the beam deflection system after an integration time of $1/f_{SNF}$ is precisely modulated in the digital-to-analog converter, dependent on a difference between a current table position (current value) and the value in the set position register.

23. Method according to claim 14, wherein a sawtooth generator that is implemented as a digital function generator is provided within the control unit.

24. Method according to claim 23, wherein the sawtooth generator is comprised of a DDS phase generator, a back-coupled digital accumulator with a start point register and step register, and a fast digital-to-analog converter.

25. Method according to claim 24, wherein the DDS phase generator delivers a phase signal with an integral multiple n of the ground frequency $f_S$ synchronous to the ground frequency $f_S$.

26. Method according to claim 14, wherein the sawtooth generator generates a sawtooth signal via digital-to-analog conversion of a digital word in the accumulator, whereby this is set to the value $a_0$ of a start register for each positive flank of the pixel phase $f_S$, and is accumulated with each further flank of the phase multiple n $f_s$ of the value $\Delta a$ of the step register.

27. Method according to claim 26, wherein an ascending or a descending sawtooth are generated, depending on the direction of excursion of the table, which is enabled by adjusting for positive or negative values of $\Delta a$, and wherein a step signal with n steps results which at n>10 approximates a sawtooth signal with good precision.

28. Method according to claim 27, wherein the amplitude of the signal is digitally very precisely adjusted by selecting the value $\Delta a$.

29. Method according to claim 14, wherein a common stable quartz mother phase generator is provided, from which the phase frequency $f_{SNF}$ of the beam tracker as well as the input frequency $f_{in}$ of the DDS phase generator are derived.

30. Method according to claim 14, wherein a digital subtracter is integrated in the sawtooth generator, and wherein the start point $t_S$ of the subtracter subtracts the current value of the accumulator from value $a_0$ in the start register.

* * * * *